(12) United States Patent
Ren et al.

(10) Patent No.: US 8,275,090 B2
(45) Date of Patent: Sep. 25, 2012

(54) MULTI-MODE TOMOSYNTHESIS/MAMMOGRAPHY GAIN CALIBRATION AND IMAGE CORRECTION USING GAIN MAP INFORMATION FROM SELECTED PROJECTION ANGLES

(75) Inventors: Baorui Ren, Andover, MA (US); Andrew P. Smith, Lexington, MA (US); Zhenxue Jing, Chadds Ford, PA (US); Jay Stein, Boston, MA (US)

(73) Assignee: Hologic, Inc., Bedford, MA (US)

( * ) Notice: Subject to any disclaimer, the term of this patent is extended or adjusted under 35 U.S.C. 154(b) by 0 days.

(21) Appl. No.: 13/196,518

(22) Filed: Aug. 2, 2011

(65) Prior Publication Data

US 2012/0039437 A1 Feb. 16, 2012

Related U.S. Application Data

(63) Continuation of application No. 12/507,450, filed on Jul. 22, 2009, now Pat. No. 7,991,106.

(60) Provisional application No. 61/092,878, filed on Aug. 29, 2008.

(51) Int. Cl.
*A61B 6/04* (2006.01)

(52) U.S. Cl. ............................................ 378/37; 378/21

(58) Field of Classification Search .................. 378/21, 378/37
See application file for complete search history.

(56) References Cited

U.S. PATENT DOCUMENTS

| | | | |
|---|---|---|---|
| 3,502,878 A | 3/1970 | Stewart | |
| 3,863,073 A | 1/1975 | Wagner | |
| 3,971,950 A | 7/1976 | Evans et al. | |
| 4,160,906 A | 7/1979 | Daniels et al. | |
| 4,310,766 A | 1/1982 | Finkenzeller et al. | |
| 4,496,557 A | 1/1985 | Malen et al. | |
| 4,559,641 A | 12/1985 | Caugant et al. | |
| 4,706,269 A | 11/1987 | Reina et al. | |
| 4,744,099 A | 5/1988 | Huettenrauch et al. | |
| 4,773,086 A | 9/1988 | Fujita et al. | |
| 4,821,727 A | 4/1989 | Levene et al. | |
| 4,969,174 A | 11/1990 | Scheid et al. | |
| 4,989,227 A | 1/1991 | Tirelli et al. | |
| 5,018,176 A | 5/1991 | Romeas et al. | |
| RE33,634 E | 7/1991 | Yanaki | |
| 5,029,193 A | 7/1991 | Saffer | |
| 5,051,904 A | 9/1991 | Griffith | |
| 5,078,142 A | 1/1992 | Siczek et al. | |
| 5,163,075 A | 11/1992 | Lubinsky et al. | |
| 5,164,976 A | 11/1992 | Scheid et al. | |
| 5,199,056 A | 3/1993 | Darrah | |
| 5,240,011 A | 8/1993 | Assa | |
| 5,289,520 A | 2/1994 | Pellegrino et al. | |
| 5,359,637 A | 10/1994 | Webber | |
| 5,365,562 A | 11/1994 | Toker | |
| 5,415,169 A | 5/1995 | Siczek et al. | |
| 5,426,685 A | 6/1995 | Pellegrino et al. | |
| 5,452,367 A | 9/1995 | Bick et al. | |
| 5,506,877 A | 4/1996 | Niklason et al. | |
| 5,526,394 A | 6/1996 | Siczek et al. | |

(Continued)

FOREIGN PATENT DOCUMENTS

EP 0775467 A1 5/1997

(Continued)

*Primary Examiner* — Alexander H Taningco
(74) *Attorney, Agent, or Firm* — Cooper & Dunham LLP

(57) ABSTRACT

A multi-mode tomosynthesis/mammography system and method in which a mammography gain map is used to gain correct mammographic images of a patient's breast but enhanced gain maps for respective projection angled are used to correct tomosynthesis images acquired with the same system.

32 Claims, 5 Drawing Sheets

U.S. PATENT DOCUMENTS

| | | |
|---|---|---|
| 5,539,797 A | 7/1996 | Heidsieck et al. |
| 5,553,111 A | 9/1996 | Moore et al. |
| 5,592,562 A | 1/1997 | Rooks |
| 5,594,769 A | 1/1997 | Pellegrino et al. |
| 5,596,200 A | 1/1997 | Sharma et al. |
| 5,598,454 A | 1/1997 | Franetzke et al. |
| 5,609,152 A | 3/1997 | Pellegrino et al. |
| 5,627,869 A | 5/1997 | Andrew et al. |
| 5,668,889 A | 9/1997 | Hara |
| 5,719,952 A | 2/1998 | Rooks |
| 5,735,264 A | 4/1998 | Siczek et al. |
| 5,769,086 A | 6/1998 | Ritchart et al. |
| 5,803,912 A | 9/1998 | Siczek et al. |
| 5,818,898 A | 10/1998 | Tsukamoto et al. |
| 5,828,722 A | 10/1998 | Ploetz et al. |
| 5,872,828 A | 2/1999 | Niklason et al. |
| 5,878,104 A | 3/1999 | Ploetz |
| 5,896,437 A | 4/1999 | Ploetz |
| 5,986,662 A | 11/1999 | Argiro et al. |
| 6,005,907 A | 12/1999 | Ploetz |
| 6,022,325 A | 2/2000 | Siczek et al. |
| 6,075,879 A | 6/2000 | Roehrig et al. |
| 6,091,841 A | 7/2000 | Rogers et al. |
| 6,137,527 A | 10/2000 | Abdel-Malek et al. |
| 6,141,398 A | 10/2000 | He et al. |
| 6,149,301 A | 11/2000 | Kautzer et al. |
| 6,175,117 B1 | 1/2001 | Komardin et al. |
| 6,196,715 B1 | 3/2001 | Nambu et al. |
| 6,216,540 B1 | 4/2001 | Nelson et al. |
| 6,219,059 B1 | 4/2001 | Argiro |
| 6,233,473 B1 | 5/2001 | Shepherd et al. |
| 6,243,441 B1 | 6/2001 | Zur |
| 6,256,370 B1 | 7/2001 | Yavuz |
| 6,272,207 B1 | 8/2001 | Tang |
| 6,289,235 B1 | 9/2001 | Webber et al. |
| 6,292,530 B1 | 9/2001 | Yavus et al. |
| 6,327,336 B1 | 12/2001 | Gingold et al. |
| 6,341,156 B1 | 1/2002 | Baetz et al. |
| 6,375,352 B1 | 4/2002 | Hewes et al. |
| 6,375,353 B1 | 4/2002 | Van Es |
| 6,411,836 B1 | 6/2002 | Patel et al. |
| 6,415,015 B2 | 7/2002 | Nicolas et al. |
| 6,442,288 B1 | 8/2002 | Haerer et al. |
| 6,459,925 B1 | 10/2002 | Nields et al. |
| 6,556,655 B1 | 4/2003 | Chichereau et al. |
| 6,597,762 B1 | 7/2003 | Ferrant et al. |
| 6,611,575 B1 | 8/2003 | Alyassin et al. |
| 6,620,111 B2 | 9/2003 | Stephens et al. |
| 6,626,849 B2 | 9/2003 | Huitema et al. |
| 6,633,674 B1 | 10/2003 | Barnes et al. |
| 6,638,235 B2 | 10/2003 | Miller et al. |
| 6,647,092 B2 | 11/2003 | Eberhard et al. |
| 6,744,848 B2 | 6/2004 | Stanton et al. |
| 6,748,044 B2 | 6/2004 | Sabol et al. |
| 6,751,285 B2 | 6/2004 | Eberhard et al. |
| 6,758,824 B1 | 7/2004 | Miller et al. |
| 6,813,334 B2 | 11/2004 | Koppe et al. |
| 6,879,660 B2 | 4/2005 | Dhawale et al. |
| 6,882,700 B2 | 4/2005 | Wang et al. |
| 6,885,724 B2 | 4/2005 | Li et al. |
| 6,912,319 B1 | 6/2005 | Barnes et al. |
| 6,940,943 B2 | 9/2005 | Claus et al. |
| 6,978,040 B2 | 12/2005 | Berestov |
| 6,999,554 B2 | 2/2006 | Mertelmeier |
| 7,110,490 B2 | 9/2006 | Eberhard et al. |
| 7,123,684 B2 | 10/2006 | Jing et al. |
| 7,127,091 B2 | 10/2006 | Op De Beek et al. |
| 7,142,633 B2 | 11/2006 | Eberhard et al. |
| 7,245,694 B2 | 7/2007 | Jing et al. |
| 7,283,857 B1 | 10/2007 | Fallon et al. |
| 7,303,643 B2 | 12/2007 | Jeromin et al. |
| 7,304,308 B2 | 12/2007 | Cheung et al. |
| 7,315,607 B2 | 1/2008 | Ramsauer |
| 7,319,734 B2 | 1/2008 | Besson et al. |
| 7,319,735 B2 | 1/2008 | Defreitas et al. |
| 7,323,692 B2 | 1/2008 | Rowlands et al. |
| 7,352,887 B2 | 4/2008 | Besson |
| 7,406,150 B2 | 7/2008 | Minyard et al. |
| 7,430,272 B2 | 9/2008 | Jing et al. |
| 7,443,949 B2 | 10/2008 | Defreitas et al. |
| 7,532,706 B2 | 5/2009 | Kameshima et al. |
| 7,850,367 B2 | 12/2010 | Takenaka et al. |
| 2001/0038681 A1 | 11/2001 | Stanton et al. |
| 2002/0012450 A1 | 1/2002 | Tsujii |
| 2002/0050986 A1 | 5/2002 | Inoue et al. |
| 2003/0018272 A1 | 1/2003 | Treado et al. |
| 2003/0073895 A1 | 4/2003 | Nields et al. |
| 2003/0095624 A1 | 5/2003 | Eberhard et al. |
| 2003/0194050 A1 | 10/2003 | Eberhard et al. |
| 2003/0194051 A1 | 10/2003 | Wang et al. |
| 2003/0194121 A1 | 10/2003 | Eberhard et al. |
| 2003/0210254 A1 | 11/2003 | Doan et al. |
| 2003/0215120 A1 | 11/2003 | Uppaluri et al. |
| 2004/0066884 A1 | 4/2004 | Hermann Claus et al. |
| 2004/0094167 A1 | 5/2004 | Brady et al. |
| 2004/0101095 A1 | 5/2004 | Jing et al. |
| 2004/0109529 A1 | 6/2004 | Eberhard et al. |
| 2004/0171986 A1 | 9/2004 | Tremaglio, Jr. et al. |
| 2004/0267157 A1 | 12/2004 | Miller et al. |
| 2005/0049521 A1 | 3/2005 | Miller et al. |
| 2005/0063509 A1 | 3/2005 | DeFreitas et al. |
| 2005/0078797 A1 | 4/2005 | Danielsson et al. |
| 2005/0105679 A1 | 5/2005 | Wu et al. |
| 2005/0113681 A1 | 5/2005 | DeFreitas et al. |
| 2005/0113715 A1 | 5/2005 | Schwindt et al. |
| 2005/0120172 A1 | 6/2005 | Mertelmeier |
| 2005/0135555 A1 | 6/2005 | Claus et al. |
| 2005/0135664 A1 | 6/2005 | Kaufhold et al. |
| 2005/0226375 A1 | 10/2005 | Eberhard et al. |
| 2006/0030784 A1 | 2/2006 | Miller et al. |
| 2006/0098855 A1 | 5/2006 | Gkanatsios et al. |
| 2006/0129062 A1 | 6/2006 | Nicoson et al. |
| 2006/0155209 A1 | 7/2006 | Miller et al. |
| 2006/0180771 A1 | 8/2006 | Jing et al. |
| 2006/0291618 A1 | 12/2006 | Eberhard et al. |
| 2007/0030949 A1 | 2/2007 | Jing et al. |
| 2007/0223651 A1 | 9/2007 | Wagenaar et al. |
| 2007/0225600 A1 | 9/2007 | Weibrecht et al. |
| 2007/0242800 A1 | 10/2007 | Jing et al. |
| 2008/0019581 A1 | 1/2008 | Gkanatsios et al. |
| 2008/0045833 A1 | 2/2008 | Defreitas et al. |
| 2008/0130979 A1 | 6/2008 | Ren et al. |
| 2009/0003519 A1 | 1/2009 | Defreitas et al. |

FOREIGN PATENT DOCUMENTS

| | | |
|---|---|---|
| EP | 0982001 A1 | 3/2000 |
| EP | 1428473 A2 | 6/2004 |
| WO | WO 90/05485 | 5/1990 |
| WO | WO 98/16903 | 4/1998 |
| WO | WO 00/51484 | 9/2000 |
| WO | WO 03/020114 A2 | 3/2003 |
| WO | WO 2005/051197 A1 | 6/2005 |
| WO | WO 2005/110230 A1 | 11/2005 |
| WO | WO 2005/112767 A1 | 12/2005 |
| WO | WO 2006/055830 A2 | 5/2006 |
| WO | WO 2006/058160 A2 | 6/2006 |

MULTI-MODE TOMOSYNTHESIS/MAMMOGRAPHY GAIN CALIBRATION AND IMAGE CORRECTION USING GAIN MAP INFORMATION FROM SELECTED PROJECTION ANGLES

CROSS-REFERENCE TO RELATED APPLICATIONS

This application is a Rule 1.53(b) continuation of U.S. patent application Ser. No. 12/507,450 filed Jul. 22, 2009, now U.S. Pat. No. 7,991,106 which in turn claims the benefit of U.S. Provisional Application No. 61/092,878 filed, Aug. 29, 2008, the entire contents of each of which are incorporated by reference herein.

FIELD

This patent specification is in the field of medical x-ray imaging and more specifically relates to multi-mode tomosynthesis/mammography methods and systems for imaging a patient's breast and to gain calibration and correction of breast images in such methods and systems. More specifically the patent specification relates to the generation and use of gain maps in x-ray breast imaging.

BACKGROUND

Breast cancer and other breast lesions continue to be a significant threat to women's health. X-ray mammography currently is the most widely used tool for early detection and diagnosis, and is the modality approved by the U.S. Food and Drug Administration to screen for breast cancer in women who do not show symptoms of breast disease. Breast tomosynthesis is a more recently developed modality and is expected to become more widely used, for diagnosis and possibly as a screening tool. An even more recent development is multi-modality breast imaging systems that have both mammography and tomosynthesis capabilities and can provide either or both of mammograms and tomosynthesis images of a patient's breast, in the same or different immobilizations of the breast.

A typical x-ray mammography system immobilizes a patient's breast on a breast platform that is between an x-ray source and an x-ray imaging receptor, and takes a projection x-ray image (called here a conventional mammogram or simply mammogram) using a collimated cone or pyramid or fan beam of x-rays at appropriate factors such as mA (current), kVp (voltage) or keV (energy), and msec (exposure time). In the United States, typically two views are taken of each breast, one from above (cranial-caudal, or CC, with the image plane generally at a 0° angle to the horizontal) and one from the side (mediolateral-oblique, or MLO, with the image plane at an angle of typically around 45° to the horizontal). Different typical views may be taken for other purposes or in other countries. The x-ray source typically is an x-ray tube operating at or in the neighborhood of 25-30 kVp, using a molybdenum, rhodium, or tungsten rotating anode with a focal spot of about 0.3 to 0.4 mm and, in some cases, 0.1 mm or less. An anti-scatter grid between the breast and the imager can be used to reduce the effects of x-ray scatter. The breast is compressed to reduce patient motion and also for reasons such as reducing scatter, separating overlapping structures in the breast, reducing the x-ray thickness of the imaged breast and making it more uniform, and providing more uniform x-ray exposure. Traditionally, the imager has been a film/screen unit in which the x-rays impinging on the screen generate light that exposes the film. In the last several years, mammography systems using electronic digital flat panel x-ray receptors have made significant inroads. A Selenia™ digital mammography system with such a digital flat panel x-ray receptor or imager is offered by Lorad, a division of the assignee hereof, Hologic, Inc. of Bedford, Mass. See brochure "Lorad Selenia™" Document B-BI-SEO US/Intl (5/06) copyright Hologic 2006. Digital mammography has significant advantages and in time may fully supplant film/screen systems.

Digital tomosynthesis also has made advances and the assignee hereof has exhibited breast tomosynthesis systems at trade shows and has carried out clinical testing. It is a three-dimensional process in which several two-dimensional projection views are acquired at respective different angles but at lower x-ray dose each compared to a conventional mammogram, and are reconstructed into tomosynthesis slice views that can be along any desired plane in the breast and can represent any thickness of breast tissue. For tomosynthesis, the breast is still immobilized, by compression to the same or lesser extent than in conventional mammography. See, e.g., International Application WO 2006/058160 A2 published under the Patent Cooperation Treaty on Jun. 1, 2006 and Patent Application Publication No. 2001/0038681 A1 PCT application International Publication No. WO 03/020114 A2 published Mar. 13, 2003, U.S. Pat. Nos. 7,142,633, 6,885,724, 6,647,092, 6,289,235, 5,051,904, 5,359,637, and 4,496,557, and published patent applications US 2004/0109529 A1, US 2004/0066884 A1, US 2005/0105679 A1, US 20050129172A1, and Digital Clinical Reports, Tomosynthesis, GE Brochure 98-5493, 11/98. A tomosynthesis system specifically for imaging patients' breast is disclosed in commonly owned U.S. Pat. Nos. 7,123,684 and 7,245,694. The publications identified in this patent specification are hereby incorporated by reference herein.

Further, the assignee hereof has developed multi-mode systems in which the same x-ray data acquisition equipment can be used for either or both of mammography and tomosynthesis imaging. A mammogram and tomosynthesis images can be acquired while the patient's breast remains immobilized, or they can be acquired at different times or patient's visits. One such system is known as Selenia Dimensions™ and another is known as Gemini™. See Smith, A., Fundamentals of Breast Tomosynthesis, White Paper, Hologic Inc., WP-00007, June 2008. Additional information regarding digital mammography, tomosynthesis and multi-mode systems offered by the common assignee can be found at <www.hologic.com>.

When digital flat panel x-ray imaging receptors are used, one of the practical requirements is to provide gain calibration. The imaging receptor may comprise a two-dimensional array of millions of imaging pixels, and there may be inherent differences in the response of different imaging pixels to impinging x-rays. When all imaging pixels receive the same x-ray exposure, ideally each should provide the same electrical output signal (pixel value). However, in practice this may not be the case and typically there are differences between the pixel values that different imaging pixels provide when exposed to the same x-ray input. In addition, incident x-ray intensity across the detector surface usually is non-uniform; for example, due to the "heel effect" the x-ray intensity drops along the direction from the chest wall to the nipple. To correct for differences in pixel values in response to uniform x-ray exposure, and to correct for the non-uniform x-ray intensity distribution across the x-ray imaging detector surface area, various gain calibration and image correction techniques are employed. Typically, in conventional x-ray mammography the flat panel imager is exposed to an x-ray field through a "flat-field" phantom that simulates a patient's breast but has a uniform thickness and is made of a uniform material, the differences between pixel values are recorded, and a gain correction map is generated that accounts for such differences. This can be done periodically during the service life of the flat panel x-ray receptor. The gain map is stored in the imaging system and, when x-ray images of a patient's breast are taken, software in the system corrects the acquired pixel values according to the gain map to bring them closer to the pixel values that would have been produced if all the imaging pixels had the same response to uniform exposure to x-ray energy.

For conventional mammography, usually one gain map is acquired for each viewing mode or x-ray filter mode. For use in this country, this may translate to one gain map for each of the CC and MLO views, for each of the filter modes, with possible consideration for the presence or the absence of an anti-scatter grid and for possible use of magnification. Gain calibration thus can be used to compensate for sensitivity differences between detector pixels and non-uniform x-ray field intensity given a particular physical relationship between the x-ray source and imaging detector. However, tomosynthesis imaging is characterized by a much greater number of changes in x-ray source projection angle during x-ray exposure, much lower x-ray exposure of the breast at any one of the projection angles, and other significant differences from conventional mammography imaging. As a result, gain maps typical for conventional mammography cannot be expected to work well in tomosynthesis image acquisition and image correction, particularly if the tomosynthesis projection angles may change depending on imaging protocol or decisions or preferences of the health professional in charge.

SUMMARY

In one non-limiting example of the new approach to gain calibration and image correction of breast tomosynthesis images described in this patent specification, a tomosynthesis system acquires a multiplicity of projection x-ray images T(p,n) of a calibration phantom, where "p" designates a respective one of a multiplicity of "P" first projection angles of an x-ray beam relative to the phantom and p=1, 2, 3, ..., P, "n" designates the number of repeated projection images taken at a given one of the angles and n=2, 3, 4, ..., N, and P and N are whole positive integers. The system generates at least one initial gain map G(p) for each projection angle "p" from the projection images T(p,n) for the same projection angle "p," by evaluating differences between expected and actual characteristics of pixel values in the projection images T(p,n). The system then forms one or more enhanced gain maps EG(p), using the initial gain maps G(p) in a computer-implemented process that combines selected parameters of the initial gain maps G(p).

After the gain maps EGM(p) are available and stored, the system acquires tomosynthesis x-ray images T'(p') of a patient's breast, where p' designates a respective one of a multiplicity of second projection angles P' of an x-ray beam relative to the patient's breast and p'=1, 2, 3, ..., P'. The first and second sets of projection angles may be the same or may differ in number of angles, in angular span, and in angle value. The system gain-corrects the tomosynthesis x-ray images T'(p') of the patient's breast using the enhanced gain maps EG(p) in a computer-implemented process to thereby produce gain-corrected breast images that can be further processed and displayed, e.g., to a health professional, or sent for storage and/or review to a remote location such as a PACS system.

A number of different ways of generating the enhanced gain maps and different ways of using the enhanced gain maps. In one non-limiting example, a "separate" enhanced gain map is generated for each of the second projection angles from initial gain maps for several but not all of the first projection angles. In a second example, a "single" enhanced gain map is generated from the initial gain maps for all of the first projection angles and is used to gain-correct breast images for all if the second projection angles. In a third example, a "single" gain map is generated for each of the second projection angles from the initial gain maps for all the first projection angles, but by weighting the initial gain maps differently for each of the second projection angles. In a fourth example, an "individual" enhanced gain map is generated for each of the second projection angles from only the initial gain map for the same or closest first projection angle.

Enhanced gain maps alternatively are generated more directly from the phantom projection images T(p,n), without first generating initial gain maps. For example, to generate a "separate" enhanced gain map for a given second projection angle, the phantom projection images T(p,n) for several first projection angle are combined, e.g., averaged, and the differences between expected and measured pixel values, or simply the differences between measured pixel values, are used to generate an enhanced gain map for the given second projection angle.

A table can be created and stored in a tomosynthesis and/or mammography system that contains gain map information from which a gain map appropriate for gain-correcting a breast image can be derived even in a case when the breast image is acquired at a projection angle in which no phantom images were acquired and/of the phantom images were acquired differently, e.g., with a different x-ray filter or a different set of technique factors such as kV and mAs. For example, the table can store gain maps for first projection angles that do not include a particular second projection angle at which a breast image is acquired. In that case, an enhanced gain map for gain-correcting the breast image is generated by interpolation addressing the closest first projection angles. Similar interpolation can be used when the breast image is taken with an x-ray filter or a set of technique factors that differ from those of gain map information in the table.

DETAILED DESCRIPTION OF PREFERRED EMBODIMENTS

In describing preferred embodiments, specific terminology is employed for the sake of clarity. However, this patent specification is not intended to be limited to the specific terminology so selected and it is to be understood that each specific element includes all technical equivalents that operate in a similar manner. In addition, a detailed description of known functions and configurations will be omitted when it may obscure the subject matter of the invention described in the appended claims.

Figure 1:
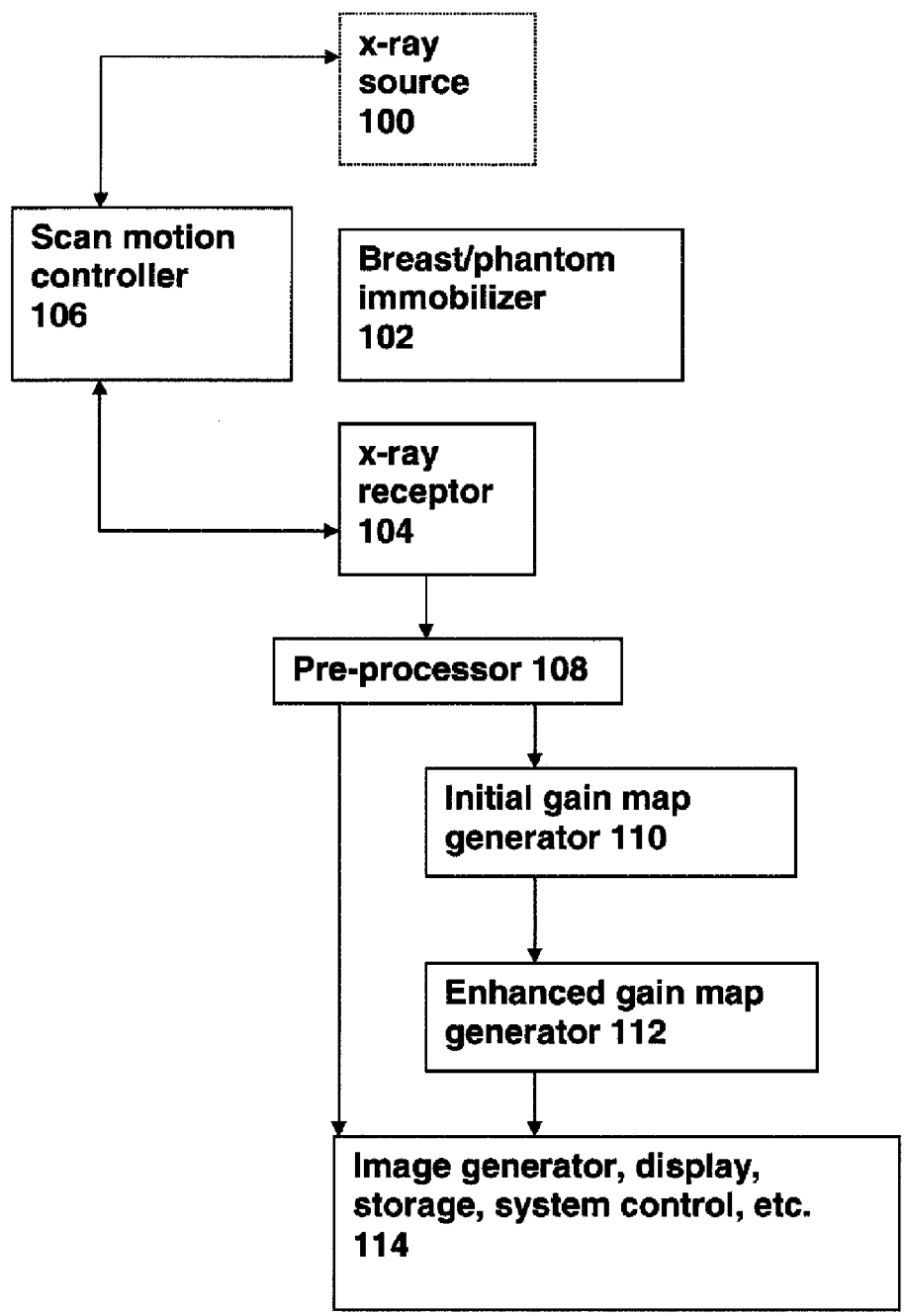
FIG. 1 illustrates in block diagram form certain components of a breast tomosynthesis system such as said Selenia Dimensions™ and Gemini™ systems developed by the assignee hereof.

Referring to FIG. 1, a multi-mode tomosynthesis/mammography gantry comprises an image acquisition unit comprising an x-ray source 100 on one side of an immobilizer 102, and an x-ray receptor 104 on the other side. Immobilizer 102 immobilizes a patient's breast or a phantom for tomosynthesis or for mammography x-ray exposures. For mammography, source 100, immobilizer 102 and receptor 104 remain in a fixed rotational relationship and move together under the control of controller 106 from one imaging position to another, e.g., from a CC position to an MLO position. For tomosynthesis data acquisition, scan motion controller 106 moves source 100 relative to immobilizer 102. Receptor 104 also moves relative to immobilizer 102 during tomosynthesis data acquisition in said Selenia Dimensions™ system but may move differently, or not at all, in other systems. Typically, the motion is motorized. The source motion can be continuous or the source can stop and emit imaging x-rays at one projection angle before moving to another projection angle. X-ray receptor 104 provides projection image data in the form of an array of pixel values related to incident x-ray energy, and can be a Selenium-based, direct conversion digital x-ray receptor available from the assignee hereof.

In the case of a calibration sequence, a calibration phantom that typically is a flat-field phantom (not shown) is secured in the immobilizer, in a position similar to that of a patient's breast when x-rays of a patient's breast are taken. To derive mammography gain maps, the system is operated in a mammography mode and x-ray projection images of the phantom are taken. Different sets of projection images can be taken for different x-ray filter and/or different technique factors. To derive tomosynthesis gain maps, the system is operated in a tomosynthesis mode and a plurality of sequences of projection images of the phantom are taken to obtain x-ray projection images $T(p,n,)$ of the phantom at each of P first projection angles within the sequence, where $n=1, 2, 3, \ldots, N$, $p=1, 2, 3, \ldots, P$, and each of P and N is a positive whole integer. Each projection x-ray image $T(p,n)$ is represented by of pixel values related to the x-rays received at respective pixel positions of an array of imaging pixels in receptor 104.

To acquire projection images of the patient, the phantom is removed and a patient's breast in immobilizer 102 is x-rayed as is known in mammography and tomosynthesis imaging sequences. A tomosynthesis sequence of a patient's breast generates projection images $T(p')$ taken at second projection angles ($p'=1, 2, 3, \ldots, P'$) that may or may not be the same in number and angle values as the first projection angles. Thus, the number of the second projection angles can be different, e.g., greater, than the number of first projection angles, and/or some or all of the second projection angles can be non-coincident with any of the first projection angles. For example, the number of second projection angles used to acquire breast images in a tomosynthesis sequence can be greater than the number of first projection angles used in acquiring phantom images, e.g., the initial gain maps $G(p)$ may be derived from phantom projection images taken at first projection angles spaced angularly by 2° over a first angular interval but tomosynthesis projection images of a patient's breast may be taken over the same angular interval but at second projection angles spaced apart by 1°. In addition, the second projection angles may range over a different or a greater angular interval than the first projection angles, and some or all of the second projection angles may not coincide with any of the first projection angles. If initial gain maps are generated from phantom images taken with different x-ray filters or at different technique factors, the breast images may be taken with filters or at technique factors that do not coincide with some or all of those used in taking the phantom images.

A workstation coupled to the acquisition unit comprises processing equipment that receives from receptor 104 (a) the projection images of the phantom taken in the mammography mode as well as the images $T(p,n)$ taken in the tomosynthesis mode of the system, and (b) the mammograms and the projection images $T(p')$ the patient's breast taken in the tomosynthesis mode of the system. The workstation preferably includes a pre-processor 108 that carries out conventional preliminary processing of the image pixel values. The mammograms and the tomosynthesis images of the patient's breast are supplied to a unit 114 from pre-processor 112 or directly from receptor 104. The phantom images are supplied to a system for generating gain maps, from pre-processor 108 if desired or directly from receptor 104. As discussed below, the gain map generator can comprise an initial gain map generator 110 that supplies its output to an enhanced map generator 112, or a generator that produced enhanced gain maps more directly from the phantom projection images. The breast images and the enhanced gain maps are supplied to a unit 114 that carries out functions such as gain-correcting the breast images using the gain calibration maps, displaying the resulting gain-corrected images, storing images and other information, providing system control, etc. Image generator 114 may also carry out other processing of the image data, such as CAD (compute-aided detection) to identify suspected abnormalities or selected other characteristics, processing to prepare images for display and to control the display, to prepare images for storage such as DICOM-compliant storage, to provide an interface for an x-ray technician or other health professional, and to provide other control functions and carry out other processing.

In a process and system for generating enhanced gain maps for gain-correcting breast images acquired in a tomosynthesis mode or operation, the phantom images $T(p,n)$ from pre-processor 110, or directly from receptor 104, are supplied to an initial gain map generator 110 that generates an initial gain map $G(p)$ for each of the P first projection angles used in acquiring the projection images $T(p,n)$, using for any given initial gain map $G(p)$ the N projection images $T(p,n)$ of the calibration phantom acquired for the same projection angle "p." Initial gain maps $G(p)$ from generator 110 are supplied to an enhanced gain map generator 112 that uses information from said initial gain maps $G(p)$ to generate one or more enhanced gain maps $EG(p')$ for use in gain-calibrating breast images that are taken or will to be taken at the second projection angles. If additional sets of phantom images $T(p,n)$ are similarly acquired but with different x-ray filters or for different technique factors, one or more tables can be created and stored to record information describing such sets of images $T(p,n)$ and/or the corresponding sets of initial gain maps $G(p)$, where each set of maps $G(p)$ pertains to a different x-ray filter or set of technique factors.

The initial gain maps $G(p)$ can be stored in the tomosynthesis system and processed in enhanced map generator 112 when needed to generate enhanced gain maps $EG(p')$ suitable for a particular tomosynthesis image acquisition of a patient's breast. Alternatively, enhanced gain maps $EG(p')$ can be generated for some of all of the breast imaging protocols of a tomosynthesis system and stored in the system for use when needed, in which case the appropriate set of enhanced gain maps EG(p') can be automatically retrieved and used upon the selection of a tomosynthesis imaging protocol.

In a first example, a separate enhanced gain map EG(p') is generated for each respective one of the second projection angles, using information derived from several but not all of the initial gain maps G(p). As a non-limiting example, information from three initial gain maps G(p) is used to generate a given enhanced gain map EG(p'). Preferably, a given enhanced gain map EG(p') is generated using information from the several initial gain maps G(p) that are for projection angles closest to that for the given enhanced gain map EG(p'). In this process, the information from the several initial gain maps can be averaged, with or without normalization, or different weighting factors can be applied to the information from the initial gain maps for different first projection angles. Most weight can be accorded to the initial gain map G(p) for the first projection angle closes to the projection angle for the given enhanced gain map EG(p'). Thus, generating a given enhanced gain map EG(p') can involve combining information in processes that include averaging, interpolation, and applying weighting factors to information derived from initial gain maps G(p).

In a second example, information from all of the initial gain maps G(p) is used in generating a single enhanced gain map EG(p'), and this single enhanced gain map is used for gain-correcting all of the breast projection images T(p'). To generate the single enhanced map, the information from the initial gain maps can be averaged, with or without normalization, or different weighting factors can be applied to the different initian gain maps.

In a third example, information from all of the initial gain maps is used to generating each of the enhanced gain maps, but for any one of the enhanced gain maps the information from initial gain maps for different first projection angles is weighted differently. As a non-limiting example, the greatest weight can be accorded to information from the initial gain map for a first projection angle that is closest to the projection angle for a given enhanced gain map, and decreasing weights are applied to information from initial gain maps for first projection angles that are progressively further from the projection angle for the given enhanced weight map.

In a fourth example, an individual enhanced gain map EG(p') is generated for each respective second projection angle from information derived only from a single initial map G(p). In this case, preferably the map G(p) is for the first projection angle that is closest to the projection angle for the given enhanced gain map EG(p').

In any of these examples, further interpolation can be carried out in generating an enhanced gain map EG(p') if sets of initial gain maps G(p) are available for different x-ray filters or sets of technique factors, to thereby generate an enhanced gain map EG(p') appropriate for the x-ray filter or set of technique factors that will be used for breast images T(p'), using techniques such as interpolation.

Figure 2:
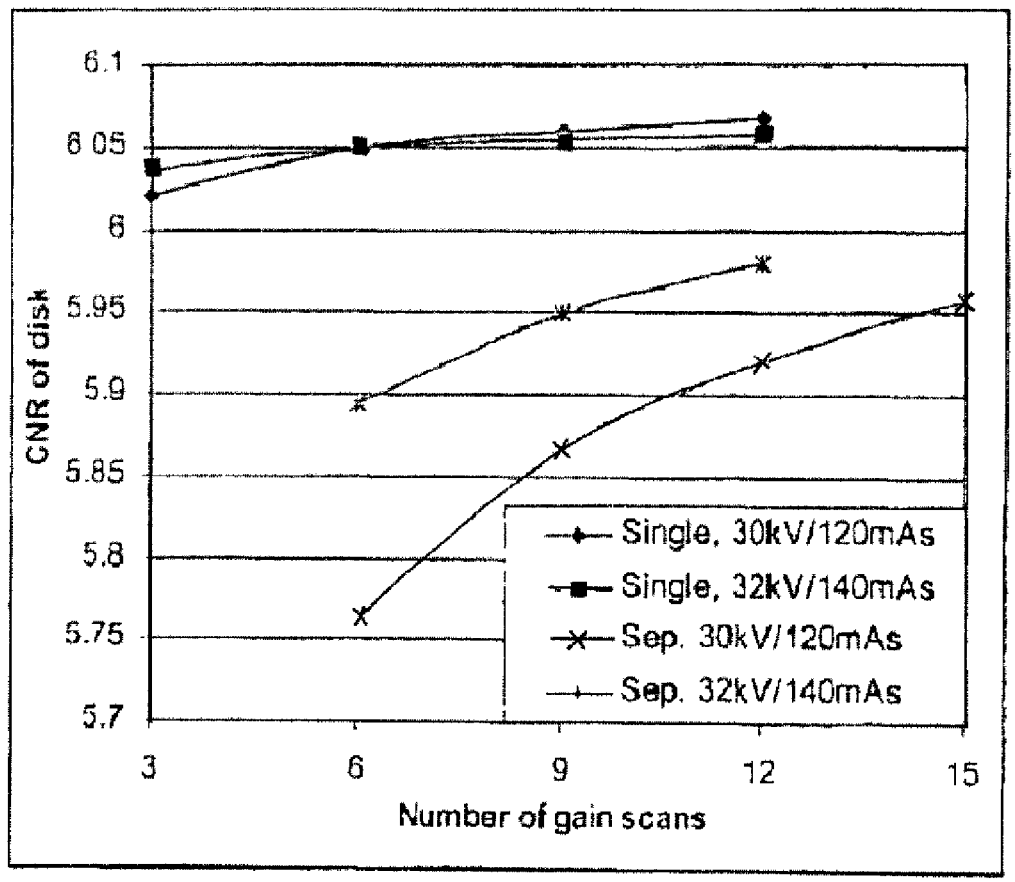
FIG. 2 illustrates graphs of CNR of a tomosynthesis projection image vs. number of scans of a gain calibration phantom used to generate different gain maps according to one disclosed embodiment.
Figure 3:
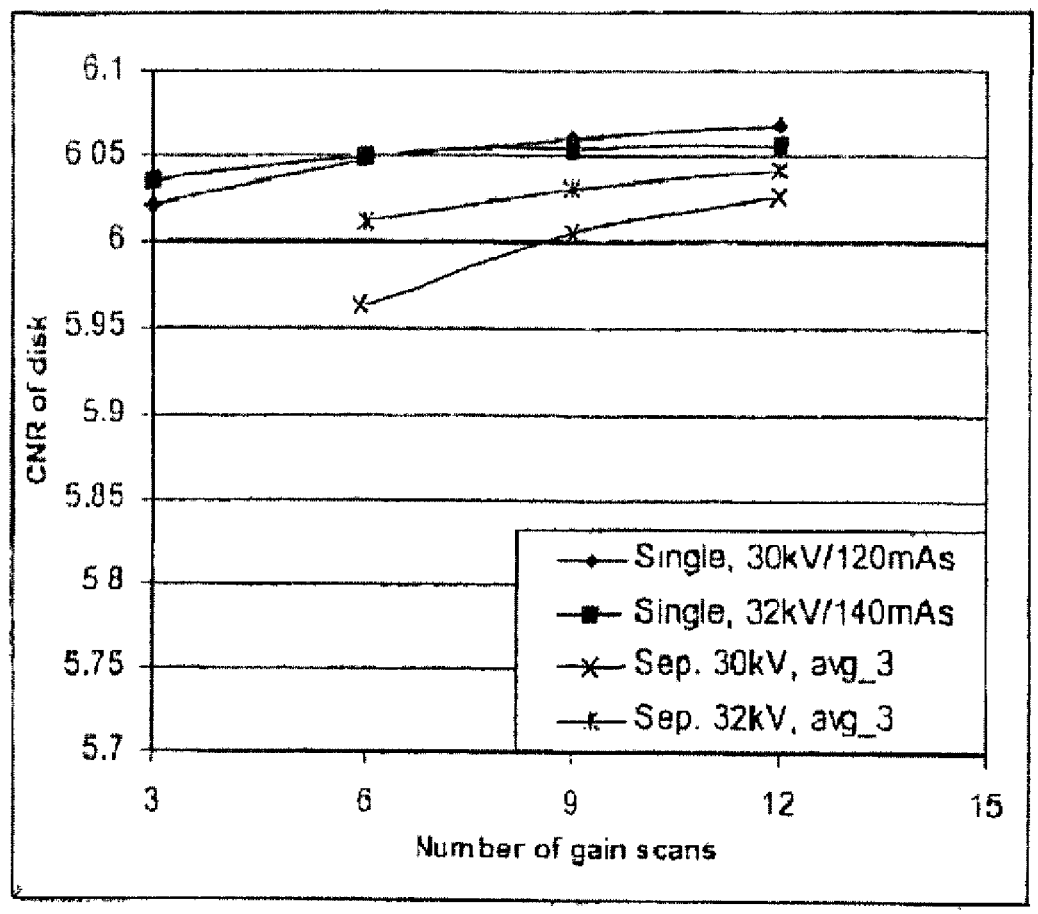
FIG. 3 illustrates graphs of CNR of a tomosynthesis projection image vs. number of scans of a gain calibration phantom used to generate different gain maps according to another disclosed embodiment.
Figure 4:
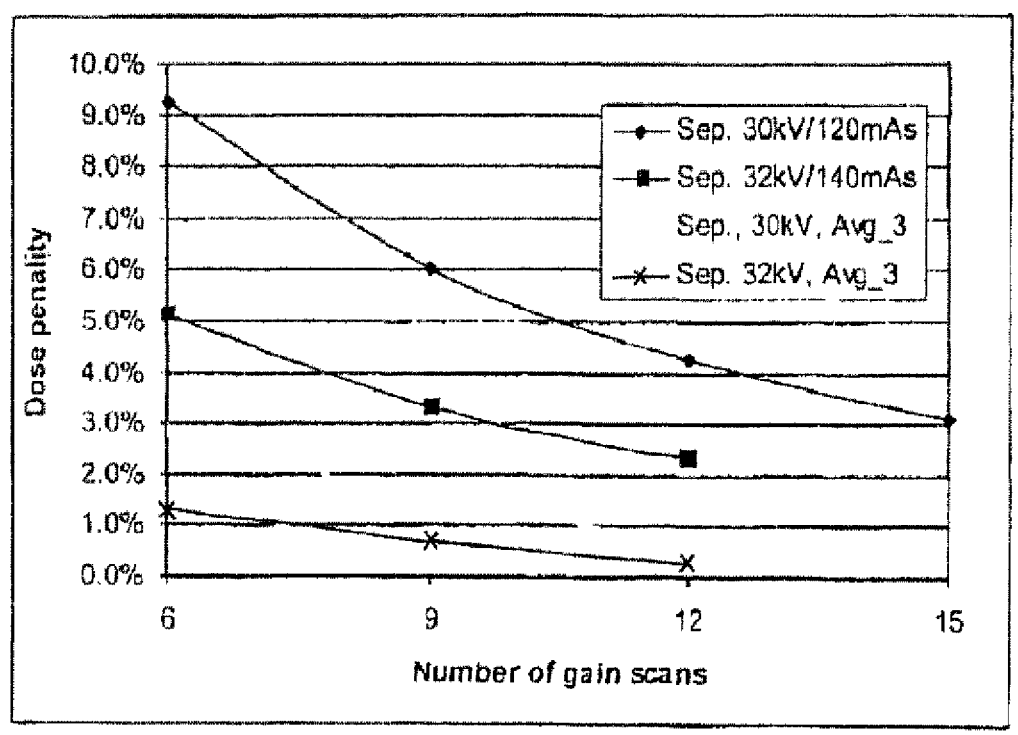
FIG. 4 illustrated graphs of x-ray dose penalty vs. number of scans when using differently generated gain maps.

FIGS. 2-4 illustrate effects and benefits of using certain examples of gain maps on CNR (Contrast Noise Ratio) of projection images of a phantom simulating a patient's breast and on x-ray dose. The projection images are of an ACR phantom, taken with a prototype multi-mode tomosynthesis/mammography system. The phantom is made to simulate a 4.2 cm compressed breast of average glandular/adipose composition, and is sold by CIRS Inc. of Norfolk, Va., and is identified as Model 015, Mammographic Accreditation Phantom. Further information regarding the phantom is available at http://www.cirsinc.com/pdfs/015 cp.pdf.

FIG. 2 shows a set of curves illustrating differences in CNR between projection x-ray images of an ACR phantom that are gain-corrected with different examples of enhanced gain maps EG(p'). Once an appropriate enhanced gain map EG(p') has been generated, the gain correction of an ACR phantom image comprises combining the image with the enhanced gain map EG(p') to convert the pixel values of the ACR phantom image to those that would have been acquired if all the imaging pixels in the x-ray receptor produced the same pixel values when exposed to a uniform x-ray field at the appropriate x-ray filter and kV and mAs parameters. The top two curves in FIG. 2 show CNR values of a projection image of an ACR phantom that was gain-corrected with a "single" enhanced gain maps generated by averaging the initial gain maps generated from all images of a flat-field phantom from all of the indicated numbers of tomosynthesis scans of that phantom. For example, the left-most data point in the curve labeled "Single, 30 kV/120 mAs" was obtained by gain-correcting an ACR phantom image taken at an appropriate projection angle with an enhanced gain map generated by averaging the initial gain maps obtained from imaging a flat-field phantom in three different tomosynthesis scans through 15 projection angles (or, alternatively, averaging the gain calibration phantom images T(p,n), three of which were taken at each of 15 projection angle, and generating an initial gain map G(p) from the averaged images T(p,n)).

An initial gain map is obtained by taking a projection image of a gain calibration phantom that typically is a uniform ("flat-field") phantom that should generate the same pixel value from each pixel in an ideal x-ray receptor and x-ray source. The initial gain map represents the differences between the actual measured pixel values and is an array of factors that, when combined with the actual measured pixel values, would produce a gain corrected image in which all pixel values are the same.

Each of the two lower curves in FIG. 2 show CNR values of a projection image of an ACR phantom that was gain-corrected with a "separate" enhanced gain map generated by averaging the initial gain maps obtained from the indicated numbers of images taken using a flat-field phantom at the given projection angle (rather than at all projection angles) and at the indicated kV and mAs parameters. For example, the leftmost data point in the curve labeled "Sep. 30 kV/120 mAs" was obtained by gain-correcting an ACR phantom image taken at a given projection angle with a gain map generated from six projection images of a flat-field phantom at the given projection angle.

As seen in FIG. 2, the CNR of a gain-corrected projection image of an ACR phantom gradually improves when using separate initial gain maps, one for each projection angle, generated from a greater number of images of a flat-field phantom. The CNR of a gain-corrected ACR phantom image improves dramatically when using a "single" gain map generated from all images of flat-field phantom. Specifically, the curve labeled "Sep. 30 kV/120 mAs" represents CNR values of a projection image of an ACR phantom gain-corrected with an enhanced gain map derived from the indicated numbers of projection images of a flat-field phantom taken at the same projection angle, at the indicated kV and mAs x-ray parameters. This curve has the lowest CNR. The curve labeled "Sep. 32 kV/140 mAs" represents CNR values of the same projection image of an ACR phantom that was gain corrected with a gain map similarly derived but at the indicated higher kV and mAs x-ray parameters, and has higher CNR values for comparable number of averaged initial gain maps. When an enhanced gain map generated from the flat-field images for all projection angles is used, the gain-corrected ACR phantom projection image has a significantly higher CNR, as shown by the curves labeled "Single, 30 kV/120 mAs" and "Single, 32 kV/140 mAs," and is relatively insensitive to the number of tomosynthesis scans used to acquire the flat-field phantom images. These top two curves differ in the x-ray parameters that were used but show similar CNR characteristics, unlike the two lower curves in FIG. 2. While a single gain map method as indicated has the best CNR results and the method requires relatively smaller number of gain scan measurements, an issue in this method is an overall image non-flatness in the gain corrected images, which can degrade image quality of clinical images.

FIG. 3 shows two top curves labeled "Single, 30 kV/120 mAs" and "Single, 32 kV/140 mAs" that are the same as those similarly labeled in FIG. 2 and were obtained similarly. The two lower curves in FIG. 3 were obtained in a different manner. Each shows the CNR values of a projection image of an ACR phantom that has been gain-corrected with an enhanced gain map derived by averaging the indicated numbers of initial gain maps for a given projection angle and the indicated number of initial gain maps for the two closest neighbor projection angles. Thus, the curve in FIG. 3 labeled "Sep. 30 kV, avg_3" shows CNR values for a projection image of a ACR phantom, taken at a given projection angle, that has been gain-corrected with an enhanced gain map generated by averaging the indicated numbers of initial gain maps for the given projection angle with those for the two closed neighbor projection angles, for the indicated 30 kV and 120 mAs. For example, the enhanced gain map for projection angle 9 is generated by averaging the initial gain maps for projection angles 8, 9 and 10. As seen in FIG. 3, the CNR for the gain-corrected ACR phantom images in two lower curves approach the CNR for the two top curves, in contrast to the case in FIG. 2. Comparing the lowest CNR curves in FIGS. 2 and 3 they shows the unexpectedly large improvement in CNR when using for gain correction an enhanced gain maps generated from the initial gain maps for only three projection angles. Because the information used for an enhanced gain map for a given projection angle comes from images taken at the same and similar projection angles, rather than from all projection angles, the enhanced gain maps provide gain correction that is believed to be more suitable for gain correcting a breast image taken at that projection angle and to help with overall image flatness.

In the alternative, instead of averaging initial gain maps for a given projection angle to obtain a data point in the lower two curves of FIG. 2, the several projection images of a flat-field phantom taken at that projection angle can be averaged into a single image for that projection angle, and that single image can be used to generate an initial gain map for that projection angle. Also in the alternative, the combining of initial gain maps, or of images for use in generating an initial gain map, need not be limited to averaging. Different weights can be applied to the initial gain maps or to the images of a flat-field phantom that are being combined. As a non-limiting example, the initial gain maps for a given projection angle can be given a higher weight than those for the neighboring projection angles in generating an enhanced gain map for the given projection angle. As another non-limiting example, the initial gain maps for a given projection angle can be given a lower weight (or even zero) than those for the neighboring projection angles in generating an enhanced gain map for the given projection angle.

FIG. 4 illustrates the effects of different gain correction approaches on the dose penalty involved in obtaining the gain maps. The term dose penalty here refers top the increase in x-ray dose needed (the penalty) to achieve the same CNR from the "separate" gain map method as from the "single" gain map method. The vertical axis is "Dose penalty," which is a parameter related to the extra x-ray dose needed in generating the separate gain maps used to gain correct ACR projection images to get the same CNR results as the single gain map. The two lower curves in FIG. 4 show x-ray dose for the conditions of the two lower curves in FIG. 3 and have the same labels. The two upper curves in FIG. 4 show x-ray dose for the conditions of the two lower curves in FIG. 2 and have the same labels. FIG. 4 illustrates that, unexpectedly, significantly lower x-ray dose penalty is involved in gain correcting an ACR phantom image taken at a given projection angle using an enhanced gain map generated from initial gain maps for that angle and initial gain maps for two neighboring projection angles.

Initial gain maps for three projection angles have been combined in order to generate an enhanced projection map for one of those angles in the example discussed above, but it should be clear that this is a non-limiting example. Initial gain maps for a different number of projection angles can be combined in generating a single enhanced gain map. Besides, different weight factors can be applied to different initial gain map to get the final enhanced gain map at each view angle. Further, while 15 projection angles may be used in the examples discussed in this patent specification, again this is only a non-limiting example, and a greater or a lesser number of projection angles can be used in a particular tomosynthesis data acquisition sequence, and the same or a different number of enhanced gain maps may be used in order to gain-correct projection images of the patient's breast obtained in that sequence. Images acquired at a few neighboring view angles could share the same enhanced gain map generated for that view angle range.

An implementation of gain map generation may be appreciated from the following description. Assume that a tomosynthesis scan uses a total of "P" projection angles, where p=1, 2, . . . , P is an index for a given projection angle. G(p) is an initial gain map for projection angle "p" so that P gain maps G(p) are generated. Each initial gain map may be generated from several projection images of a flat-field phantom at the same projection angle, e.g., six such images. For each projection angle in the range p=2 through p=P−1, an enhanced gain map EG(p) is generated as a combination (e.g., an average) of G(p−1), G(p) and G(p+1). For angle p=1 the enhanced gain map EG(1) is generated as a combination of G(1), G(2) and G(3). For angle P, the enhanced gain map is generated from gain maps G(P−2), G(P−1) and G(P).

While the example described immediately above uses initial gain maps for three projection angles to generate an enhanced gain map for a single projection angle, using a different number is possible. For example, a parameter "D" can be made configurable by service personnel or by a user of the system to set the number N=2D+1 of projection angles that contribute information to an enhanced gain map. In the example of a multi-mode system that uses a total of 15 projection angles in a tomosynthesis image data acquisition sequence, the parameter D may be defaulted to D=1 in programming the system, in which case N=2+1=3, as in the example described immediately above. However, parameter D may be made configurable to 0=<D<7 in the example where P=15. When D=0, only the initial gain map for one projection angle is used to gain correct clinical images of the tomosynthesis system taken at the same or the closest projection angle. When D=1, only initial gain maps for a given projection angle and two nearest neighbors would be used to generate an enhanced gain map for that angle. When D=6, the enhanced gain map for a given projection angle can be generated from the initial gain map for that (or the closest) projection angle and the initial gain map for its nearest 12 projection angles. The combination of initial gain maps to generate the enhanced gain map can take the mathematical form of simple averaging, or weighted averaging, with user configurable different weight factors allowed.

Figure 5:
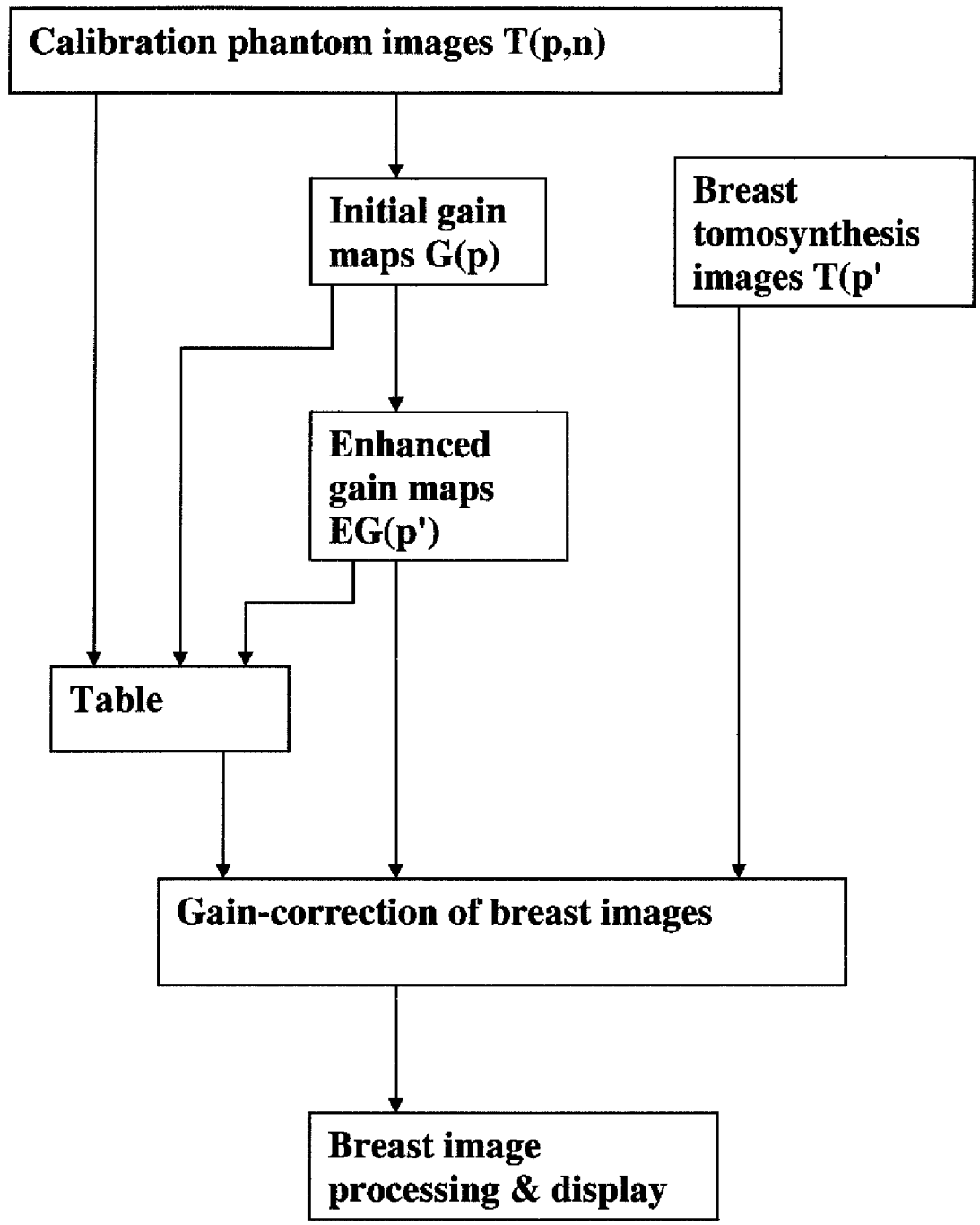
FIG. 5 illustrates an example of information flow in generating gain map information and gain-correcting tomosynthesis breast images.

FIG. 5 illustrates information flow in a process and system according to the description above. As illustrated, the images T(p,n) of a calibration phantom can be supplied to a process for generating initial gain maps (G(p), or they can be supplied and stored in a Table. The initial gain maps can be supplied to a process for generating enhanced gain maps EG(p'), or they also can be supplied to and stored in the Table. The enhanced gain maps also can be supplied to and stored in the Table. A gain-correction process receives breast tomosynthesis images T(p'), and gain-corrects them using any one of (a) enhanced gain maps directly from the process that generated them, (b) enchanged gain maps stored in the Table, (c) initial gain maps stored in the Table, and (d) images T(p,n) stored in the Table. To the extent interpolation is needed or desirable, the gain-correction process interpolates using information from the Table.

The foregoing of preferred embodiments has been presented as an illustration of examples and is not intended to be exhaustive or to limit the claimed inventions to the specific examples. Those examples are intended to describe principles that persons skilled in the art may use to practice the claimed inventions, using variations and modifications of the disclosed examples that are suited to a particular environment. It is intended that the scope of the invention be defined by the appended claims and their equivalents.

The invention claimed is:

1. A multi-mode breast tomosynthesis/mammography system comprising:

an image acquisition unit comprising an x-ray source, a breast immobilizer, and an x-ray image receptor, said unit acquiring projection x-ray images of an object at selected projection angles;

a scan motion controller selectively operating said system:
in a tomosynthesis mode, in which at least one of the x-ray source and the x-ray image receptor moves relative to the breast immobilizer while a patient's breast remains immobilized therein and take tomosynthesis projection images at respective angles or angle ranges of the source relative to the breast immobilizer; or
in a mammography mode, in which the x-ray source, the breast immobilizer and the x-ray image receptor maintain a fixed rotational relationship to move together under the control of the scan motion controller and take at least one mammography image;

an initial gain map generator configured to receive x-ray projection images taken with said image acquisition unit of a phantom at a multiplicity of first projection angles while said system is operating in said tomosynthesis mode, said initial gain map generator being further configured to process the projection images of the phantom received thereby and generate therefrom an initial gain map for each of said first projection angles;

an enhanced gain map generator configured to receive said initial gain maps, said enhanced map generator being further configured to process the initial gain maps received thereby and generate therefrom at least one enhanced gain map;

a mammography gain map generator configured to receive at least one mammographic image of a phantom while the system is operating in said mammography mode and to generate a mammography gain map therefrom;

an image generator configured to receive said enhanced gain maps and tomosynthesis projection x-ray images of a patient's breast taken with said image acquisition unit at a multiplicity of second projection angles while the system is operating in said tomosynthesis mode, said image generator being further configured to gain-correct said tomosynthesis breast images with said at least one enhanced gain maps to thereby generate gain-corrected tomosynthesis breast images;

said image generator being further configured said image generator being further configured to receive at least one mammography image generated while the system is operating in said mammography mode and to gain correct said mammography image with said mammography gain map to thereby generate a gain-corrected mammography image; and selectively displaying at least some of said tomosynthesis projection images, said gain-corrected tomosynthesis breast images and said gain-corrected mammography image.

2. A system as in claim 1 in which said enhanced map generator is configured to generate a single enhanced gain map and said image generator is configured to correct at least a subset of several of said tomosynthesis breast images with said single enhanced gain map.

3. A system as in claim 1 in which said enhanced map generator is configured to generate a multiplicity of different enhanced gain maps and said image generator is configured to correct each of at least a subset of several of said breast images with a different one of said enhanced gain map.

4. A system as in claim 1 in which said enhanced map generator is configured to generate a respective enhanced gain maps for each of said second projection angles and said image generator is configured to correct each of said breast images with a respective one of said enhanced gain map.

5. A system as in claim 1 in which said first projection angles and said second projection angles differ from each other, and said enhanced map generator is configured to account for said difference between the first and second projection angles in generating said at least one enhanced gain map.

6. A system as in claim 1 in which said first projection angles and said second projection angles differ from each other, and said enhanced map generator is configured to generate respective enhanced gain maps for said second projection angles by interpolation from parameters of said initial gain maps.

7. A system as in claim 6 in which said first projection angles and said second projection angles differ from each other, and said enhanced map generator is configured to generate respective preliminary enhanced gain maps for said first projection angles and process said preliminary enhanced gain maps to generate therefrom respective final enhanced maps to the second projection angles, and said image generator is configure to gain-correct said breast images with said final enhanced gain maps.

8. A system as in claim 1 in which said scan motion controller is further configured to cause said x-ray image receptor to move relative to said breast immobilizer when operating the system in said tomosynthesis mode.

9. A system as in claim 1 in which said scan motion controller is further configured to move said x-ray source and said x-ray image receptor through different ranges in angle relative to said breast immobilizer when operating the system in said tomosynthesis mode.

10. A breast x-ray imaging method comprising:
obtaining tomosynthesis projection x-ray images T(p,n) of a phantom, where the index p designates a respective one of a first multiplicity of P first projection angles of an x-ray beam relative to the phantom, p=1, 2, 3, ..., P, the index n designates the number of projection images taken at a given one of the first projection angles, and n≧2;
obtaining enhanced gain maps EG(p'), where the index p' designates a respective one of a second multiplicity of P' second projection angles of an x-ray beam relative to a patient's breast and p'=1, 2, 3, ..., P', said maps EG(p') having been generated in a computer-implemented process combining parameters derived from said images T(p,n);
storing the enhanced gain maps EG(p') in a table;
obtaining tomosynthesis x-ray images T'(p') of a patient's breast acquired at said second projection angles;
gain-correcting the tomosynthesis x-ray images T'(p') of the patient's breast using the stored enhanced gain maps EG(p') in a computer-implemented process to thereby produce gain-corrected breast images; and
further computer-processing said gain-corrected breast images to generate therefrom display breast images, and displaying said display breast images derived through said further computer-processing.

11. A method as in claim 10 in which said parameters derived from the phantom images T(p,n) comprise respective initial gain maps G(p) for said first projection angles.

12. A method as in claim 11 in which said combining comprises combining initial gain maps G(p) for P>M≧2 first projection angles to generate an enhanced gain map EG(p') for a given second projection angle.

13. A breast tomosynthesis method as in claim 12 in which M=2D+1 and D≧1.

14. A breast tomosynthesis method as in claim 13 in which D=1.

15. A breast tomosynthesis method as in claim 13 in which the value of D is selectable and changeable by a user of a tomosynthesis system carrying out said tomosynthesis method.

16. A breast tomosynthesis method as in claim 12 in which said combining comprises averaging of said initial gain maps G(p) for different ones of said first projection angles.

17. A breast tomosynthesis method as in claim 12 in which said combining comprises applying different weighting factors to different ones of said initial gain maps G(p) for different ones of said first projection angles.

18. A breast tomosynthesis method as in claim 12 in which said combining in order to generate an enhanced gain map EG(p') for a given one of said second projection angles comprises applying greater weight to an initial gain map G(p) for a first projection angle that is closer to said given one of the second projection angles than to an initial gain map G(p) for a first projection angle that is further from said given one of the second projection angles.

19. A breast tomosynthesis method as in claim 12 in which the enhanced gain map EG(p') for a given one of said second projection angle is generated by combining the initial gain maps G(p) for the M second projection angles that are nearest to the given second projection angle.

20. A breast tomosynthesis method as in claim 12 in which each of a subset of the enhanced gain maps EG(p') is for a second projection angle that does not coincide with a first projection angle and said combining to generate each enhanced gain map EG(p') of said subset comprises interpolation between values included in initial gain maps G(p) for M first projection angles.

21. A breast tomosynthesis method as in claim 12 in which said combining comprises combining initial gain maps G(p) for M=P first projection angles to generate each of said enhanced gain maps EG(p').

22. A breast tomosynthesis method as in claim 13 in which said combining comprises applying different weight factors to the initial gain maps G(p) used to generate the respective enhanced gain maps EG(p') for different ones of said second projection angles.

23. A breast tomosynthesis method as in claim 14 in which said different weighting factors are related to differences between said first projection angles and said second projection angles.

24. A breast tomosynthesis method as in claim 10 in which the generating of an enhanced gain maps EG(p') for a given one of the second projection angles comprises combining parameters derived from phantom projection images T(p,n) acquired at a single one of said first projection angles.

25. A breast tomosynthesis method as in claim 10 in which said combining comprises combining parameters derived from phantom images T(p,n) for P>M≧2 first projection angles to generate an enhanced gain map EG(p') for a given second projection angle.

26. A breast x-ray imaging method comprising:
obtaining tomosynthesis projection x-ray images of a phantom at each of a multiplicity of first projection angles of an x-ray beam relative to the phantom;
obtaining respective initial gain maps for said first projection angles wherein said initial gain maps are related to differences between expected and actual characteristics of pixel values in said projection x-ray images of the phantom;
obtaining tomosynthesis x-ray images of a patient's breast acquired for each of a multiplicity of second projection angles, wherein the second projection angles differ in number or in angle values from said first projection angles;
obtaining respective enhanced gain maps for said second projection angles, said enhanced gain maps having been generated by computer-processing parameters derived from said initial gain maps;
storing the enhanced gain maps in a table;
gain-correcting said tomosynthesis x-ray images of the patient's breast using said stored enhanced gain maps;
further computer-processing said gain-corrected breast images to generate processed breast images; and
displaying said processed breast images resulting from said further computer-processing.

27. A breast x-ray imaging method as in claim 26 in which said deriving comprises an interpolation process.

28. A breast x-ray imaging method as in claim 26 in which said second projection angles are greater in number than said first projection angles.

29. A breast x-ray imaging method as in claim 26 in which said enhanced gain maps are greater in number than said initial gain maps.

30. A breast x-ray imaging method as in claim 26 in which said enhanced gain map for a given second projection angle is derived in a computer-implemented process that comprises using parameters of at least one initial gain map for a projection angle that is closest in angle value to the given second projection angle.

31. A breast x-ray imaging method as in claim 26 in which said tomosynthesis x-ray images of the patient's breast are obtained in a process that comprises selecting the number of said second projection angles by a user of a tomosynthesis system carrying out the method.

32. A method of operating a tomosynthesis system comprising:
- acquring tomosynthesis projection x-ray images of a phantom, where at least one phantom projection image is acquired for each of a multiplicity of different first projection angles relative to the phantom;
- generating initial tomosynthesis gain maps for said first projection angles using said tomosynthsis projection images of the phantom;
- forming at least one enhanced tomosynthesis gain map by combining at least some of the initial tomosynthsis gain maps;
- operating the system to acquire tomosynthesis x-ray images of a patient's breast at a multiplicity of second projection angles; and
- selectively displaying the resulting gain-corrected mammogram images and/or tomosynthesis images.

* * * * *